United States Patent [19]

Schmitt-Willich et al.

[11] Patent Number: 5,733,522
[45] Date of Patent: Mar. 31, 1998

[54] DERIVATIZED DTPA COMPLEXES, PHARMACEUTICAL AGENTS CONTAINING THESE COMPOUNDS, THEIR USE AND PROCESS FOR THEIR PRODUCTION

[75] Inventors: Heribert Schmitt-Willich; Johannes Platzek; Heinz Gries; Bernd Radüchel; Orlin Petrov; Andreas Mühler; Thomas Frenzel; Hubert Vogler; Hans Bauer; Klaus Nickisch; Jean-Claude Hilscher, all of Berlin, Germany

[73] Assignee: Schering Aktiengesellschaft, Berlin, Germany

[21] Appl. No.: 495,473

[22] PCT Filed: Jan. 8, 1994

[86] PCT No.: PCT/EP94/00033

§ 371 Date: Sep. 29, 1995

§ 102(e) Date: Sep. 29, 1995

[87] PCT Pub. No.: WO94/17029

PCT Pub. Date: Aug. 4, 1994

[30] Foreign Application Priority Data

Jan. 25, 1993 [DE] Germany .................. 43 02 287.1

[51] Int. Cl.$^6$ .................. A61B 5/055; A61K 49/04
[52] U.S. Cl. .................. 424/1.65; 424/9.364; 424/9.365; 424/9.42; 424/9.5; 514/492; 514/502; 514/836; 436/173; 534/16
[58] Field of Search .................. 424/9.364, 9.365, 424/9.42, 1.65, 9.5; 514/492, 502, 836; 436/173; 128/653.4, 654; 534/16

[56] References Cited

U.S. PATENT DOCUMENTS

| | | | |
|---|---|---|---|
| 4,647,447 | 3/1987 | Gries et al. | 424/9.36 |
| 4,880,008 | 11/1989 | Lauffer | 424/9.361 |
| 5,021,571 | 6/1991 | Mease et al. | 544/166 |
| 5,039,512 | 8/1991 | Kraft et al. | 424/9 |
| 5,089,663 | 2/1992 | Mease et al. | 562/507 |
| 5,316,756 | 5/1994 | Gries et al. | 424/9.365 |
| 5,399,340 | 3/1995 | Radüchel et al. | 424/9 |
| 5,482,700 | 1/1996 | Deutsch et al. | 424/9.364 |

FOREIGN PATENT DOCUMENTS

| | | |
|---|---|---|
| 713093 | 7/1965 | Canada . |
| 0230893 | 8/1987 | European Pat. Off. . |
| 0405704 | 1/1991 | European Pat. Off. . |
| 1 155 122 | 10/1963 | Germany . |
| 91/14459 | 10/1991 | WIPO . |
| 94/27644 | 12/1994 | WIPO . |
| 95/15319 | 6/1995 | WIPO . |

*Primary Examiner*—Gary E. Hollinden
*Attorney, Agent, or Firm*—Millen, White, Zelano & Branigan, P.C.

[57] ABSTRACT

The invention relates to complex compound as well as their salts consisting of at least one metal ion and one complexing agent of general formula I

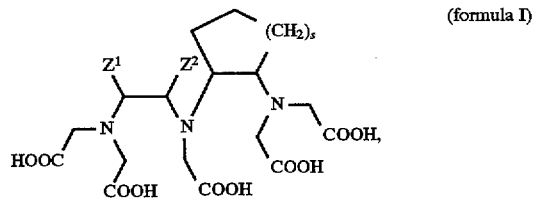

(formula I)

in which $Z^1$, $Z^2$ and s have different meanings, as well as their use for the production of agents for radiation therapy and for NMR diagnosis and diagnostic radiology, especially for contrasting the hepatobiliary system. Further, the invention relates to a process for the production of these compounds and agents.

13 Claims, No Drawings

DERIVATIZED DTPA COMPLEXES, PHARMACEUTICAL AGENTS CONTAINING THESE COMPOUNDS, THEIR USE AND PROCESS FOR THEIR PRODUCTION

This application is a 371 of PCT/EP94/00033 filed Jan. 8, 1994.

The invention relates to the object characterized in the claims, i.e. new complexes and complex salts, agents containing these compounds, their use in diagnosis and radiation therapy, as well as the process for the production of these compounds and agents.

At the beginning of the fifties, metal complexes were already under consideration as contrast media for radiology. However, the compounds used at that time were so toxic that using them in humans was out of the question. It was therefore really surprising that certain complex salts turned out to be sufficiently compatible so that routine use in humans for diagnostic purposes could be considered. As a first representative of this family of substances, the dimeglumine salt of GdDTPA (gadolinium(III) complex of diethylenetriaminepentaacetic acid; Magnevist® described in the European patent application with publication number 0 071 564 proved to be a very good contrast medium for nuclear spin tomography.

This contrast medium is especially well-suited for the diagnosis of pathological areas (e.g., inflammations, tumors, infarctions, etc.). After intravenous injection, the compound spreads extracellularly and is eliminated by glomerular secretion through the kidneys. Crossing of intact cell membranes and extrarenal elimination are practically not observed.

Also, the metal complexes described in patent applications EP 0 305 320 and EP 0 299 795 spread extracellularly and are eliminated almost exclusively renally. For the patients with limited renal function, the above-mentioned contrast media are therefore less suitable, since elimination in the case of the latter takes place only slowly, so that complete removal of the contrast medium from the organism is often successful only with the aid of a dialyzer.

Because of their pharmacokinetic behavior, these contrast media are also suitable as diagnostic agents for the hepatobiliary area only to a limited extent. Therefore, there is a need for contrast media that are taken up by the liver cells and thus make it possible to distinguish healthy parenchyma from tumorous tissue better.

Contrast media suitable for this application are described in EP 0 186 616. However, these agents based on dextran-coated, magnetic ferrous oxide particles suffer from the drawback that they unnecessarily stress the iron depot of the body. Furthermore, these compounds—as all compounds of high-molecular weight—can cause an undesirable, long-term hematoma formation in the patient in the case of inexpert injection (i.e., if the vein is missed). This danger does not exist, however, with the fast-spreading compounds of low molecular weight.

EP 0 405 704 describes metal complexes of DTPA derivatives substituted with lipophilic groups. These compounds basically show the desired elimination behavior, i.e., in addition to the renal elimination, a certain portion of the contrast medium is also eliminated with the feces, but improvement of the extrarenal/renal elimination ratio is especially desirable for use in tenally insufficient patients.

It is also important to further improve relaxivity, which can be used as a measure of the imaging effect, so that the dose necessary for a diagnostic statement can be further reduced.

Thus, the object of the invention is to provide compounds and agents that overcome the above-described drawbacks of the prior art, i.e. to find compounds (agents) which are mainly eliminated extrarenally or hepatobiliarly and whose diagnostic effectiveness is further improved, as well as to provide a process for their production.

It has now been found that this object is achieved, surprisingly enough, by complex compounds and agents containing the latter, consisting of at least one metal ion of an element of atomic numbers 21–29, 42, 44 or 58–83 and a complexing agent of general formula I

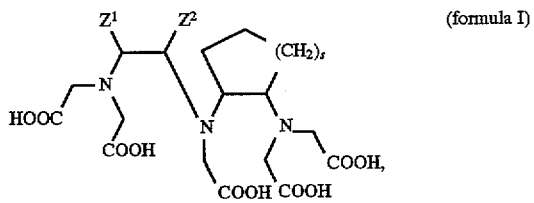

(formula I)

in which $Z^1$ and $Z^2$, independently of one another, stand for a hydrogen atom, the radical $-(CH_2)_m-(C_6H_4)_q-(O)_k-(CH_2)_n-(C_6H_4)_l(O)_r-R$, or the radical $-(CH_2)_m-(C_6H_{10})_q-(O)_k-(CH_2)_n-(C_6H_{10})_l(O)_r-R$, in which m and n mean numbers 0–5, q, k, l and r mean numbers 0 or 1 and s means numbers 1 or 2, R means a hydrogen atom, an optionally $OR_1$-substituted straight-chain or branched $C_1-C_6$ alkyl radical or a $CH_2-COOR^1$ group, in which $R^1$ means a hydrogen atom, a $C_1-C_6$ alkyl radical or a benzyl group, provided that in each case one of substituents $Z^1$ or $Z^2$ stands for a hydrogen atom and the other does not stand for hydrogen, and that a direct oxygen-oxygen bond is not allowed, in which case free carboxylic acid groups, i.e., carboxylic acid groups that are not needed to complex the metal ion of the mentioned atomic numbers, are present optionally partially or completely as a salt of an amino acid or an amino acid amide or as a salt of an inorganic or organic base.

The compounds according to the invention show to a surprisingly large extent the desired property, i.e., they are predominantly excreted by a hepatobiliary pathway, by which a visualization of the liver, gall, gallbladder, and biliary tract is possible. Furthermore, in general they show, surprisingly enough, a higher relaxivity than the structurally similar compounds of EP 0 405 704.

With the provision of the complex compounds according to the invention, in particular renally insufficient patients can thus be examined by NMRdiagnosis and diagnostic radiology.

The practical use of the new complexes is facilitated by their high chemical stability.

If the agent according to the invention is intended for use in NMR diagnosis, the central ion of the complex salt must be paramagnetic. These are in particular the divalent and trivalent ions of the elements of atomic numbers 21–29, 42, 44 and 58–70. Suitable ions are, for example, the chromium (III), manganese(II), iron(II), nickel(II), copper(II), praseodymium(III), neodymium(III), samarium(III) and ytterbium(III) ion. Because of their very strong magnetic moment, the gadolinium(III), terbium(III), dysprosium(III), holmium(III), erbium(III), and iron(III) ions are especially preferred.

If the agent according to the invention is intended for use in diagnostic radiology, the central ion has to be derived from an element of a higher atomic number to achieve adequate absorption of the x rays. It has been found that, for this purpose, diagnostic agents that contain a physiologically compatible complex salt with central ions from elements of atomic numbers between 21–29, 42, 44, 57–83 are suitable. These are, for example, the lanthanum(III) ion and the above-mentioned ions of the lanthanoid series.

The numbers standing for m and n are preferably 0–2.

As alkyl substituents R and $R^1$, straight-chain, branched, or cyclic hydrocarbons with up to 6 carbon atoms, which in the case of R are optionally substituted by one or more, preferably 1 to 3 hydroxy groups or $C_1$–$C_6$, preferably $C_1$–$C_4$ alkoxy groups, are suitable.

As optionally substituted alkyl groups, there can be mentioned, for example, the methyl, hydroxymethyl, ethyl, 2-hydroxyethyl, 2-hydroxy-1-(hydroxymethyl)-ethyl, 1-(hydroxymethyl)-ethyl, propyl, isopropyl, 2- and 3-hydroxypropyl, 2,3-dihydroxypropyl, n-, sec- and tert-butyl, 2-, 3- and 4-hydroxybutyl, 2- and 3-hydroxyisobutyl, pentyl, 2-, 3- and 4-hydroxy-2-methylbutyl, 2,3,4-trihydroxybutyl, 1,2,4-trihydroxybutyl, cyclopentyl, cyclohexyl, 2,3,4,5,6-pentahydroxyhexyl group as well as—in the case of the hydroxyalkyl groups—their $C_1$–$C_6$, preferably $C_1$–$C_4$ alkyl derivatives.

Preferred substituents $Z^1$ or $Z^2$ of the compounds according to the invention are the —$CH_2$—$CH(CH_3)_2$, —($CH_2$)$_4$—$CH_3$, —$CH_2C_6H_5$, —$CH_2$—$C_6H_4OH$, —$CH_2$—$C_6H_4$—$OCH_3$, —$CH_2$—$C_6H_4$—$OC_2H_5$, —$CH_2$—$C_6H_4$—$OC_4H_9$, —$CH_2$—$C_6H_4$—$OCH_2$—$COOH$, —$CH_2$—$C_6H_{10}$—$OC_2H_5$ and the —$CH_2$—$C_6H_4$—$O$—$CH_2$—$C_6H_4$—$OCH_3$ radical.

If not all acid hydrogen atoms are substituted by the central ion, one, several or all remaining hydrogen atom(s) can optionally be replaced by cations of inorganic and/or organic bases or amino acids. Suitable inorganic cations are, for example, the lithium ion, the potassium ion, the magnesium ion and, in particular, the calcium ion and the sodium ion. Suitable cations of organic bases are, i.a., those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, arginine, and ornithine. Suitable cations of amino acid amides are, for example, those of lysine methylamide, glycine ethylamide and serine methylamide.

The production of the complex compounds according to the invention takes place in a way known in the art, e.g., by a triamine of general formula II

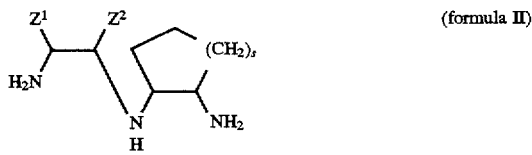

(formula II)

in which $Z^1$, $Z^2$ and s have the indicated meanings, optionally being reacted in the presence of a base, with a compound of general formula III

Y—$CH_2$—$COOR^2$ (formula III), in which

Y means a leaving group and $R^2$ means an acid protective group or a hydrogen atom, in a polar solvent at –10° C. to 170° C. within 1–100 hours, protective groups optionally being cleaved, and then the complexing agents of formula I thus obtained being complexed with a metal ion.

Any leaving group familiar to one skilled in the art can stand for leaving group Y. For example, acetate, brosylate, mesylate, nosylate, tosylate, trifluoroacetate, trifluorosulfonate, chlorine, bromine, or iodine can be mentioned. Preferred leaving groups are chlorine and bromine; bromine is especially preferred.

As acid protective groups $R^2$, lower alkyl, aryl and aralkyl groups, for example, the methyl, ethyl, propyl, n-butyl, t-butyl, phenyl, benzyl, diphenylmethyl, triphenylmethyl, bis(p-nitrophenyl)-methyl group as well as trialkylsilyl groups are suitable.

The cleavage of protective groups $R^2$ takes place according to the processes known to one skilled in the art [e.g., E. Wünsch, Methoden der Org. Chemie [Methods of Org. Chemistry] (Houben-Weyl), Vol. XV/1, 4th edition 1974, p. 315 ff], for example, by hydrolysis, hydrogenolysis or alkaline saponification of esters with alkali in an aqueous-alcoholic solution at temperatures of 0° to 80° C. Organic or inorganic acids can also be used to cleave the t-butyl esters that are especially advantageous for these reactions: the ester compound dissolved in a suitable anhydrous organic solvent, but preferably the pulverized dry substance, is mixed either with a hydrogen halide solution in glacial acetic acid, with trifluoroacetic acid or else boron trifluoride diethyl etherate in glacial acetic acid and cleaved at temperatures of –10° C. to 60° C., preferably at room temperature.

Compounds of general formula I, which in $Z^1$ or $Z^2$ contain an alkoxyphenyl radical, can also be obtained, in a way known in the art (see EP 0 405 704), by compounds of general formula IV

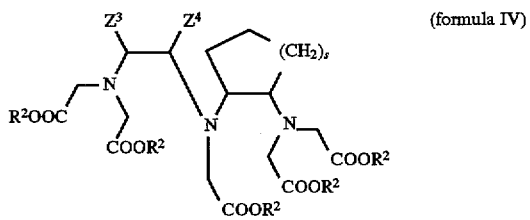

(formula IV)

in which $R^2$ and s have the indicated meanings and $Z^3$ and $Z^4$ stand, in each case, for a hydrogen atom or radical —$(CH_2)_m$—$(C_6H_4)_q$—OH, provided that one of substituents $Z^3$ and $Z^4$ stands for a hydrogen atom and the other for the indicated radical, being converted to a compound with the radicals indicated for $Z^1$ and $Z^2$, acid protective groups $R^2$ being cleaved in the above-described way, the complexing agents of general formula I thus obtained being reacted with at least one metal oxide or metal salt of an element of atomic numbers 21–29, 42, 44 or 57–83 and then optionally present acid hydrogen atoms being substituted by cations of inorganic and/or organic bases, amino acids or amino acid amides.

The above-mentioned groups are suitable as acid protective groups $R^2$.

Compounds of formula I which contain a cyclohexyl radical in $Z^1$ or $Z^2$ can be obtained from the corresponding compounds of general formula IV that carry a benzene ring in $Z^3$ or $Z^4$ by reduction, e.g., with hydrogen on rhodium contacts.

The triamines of general formula II can be obtained, e.g., by reacting the intermediate products of general formula VI—which can be produced in a way known in the art from the corresponding alcohols of formula V—with 1,2-diaminocyclopentane or—hexane to compounds of general formula VII and subsequent cleavage of the amino protective group,

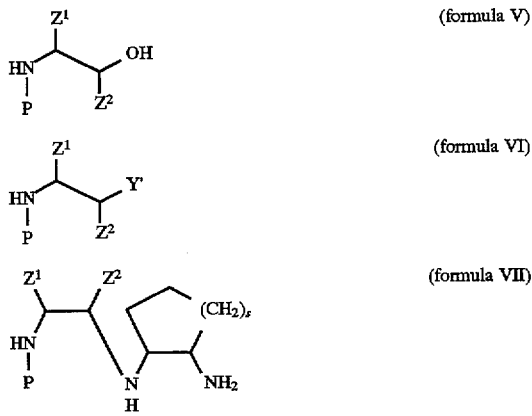

in which $Z^1$, $Z^2$ and s have the above-indicated meaning,

Y' is a leaving group and P1 stands for an amino protective group.

As leaving group Y', for example, trifluoromethylsulfonate, brosylate and nosylate, preferably tosylate and mesylate, can be mentioned.

As amino protective group P, all amino protective groups known to one skilled in the art [see, e.g., E. Wünsch, Methoden der Org. Chemie (Houben-Weyl), Volume XV/1, 4th edition 1974, p. 46 ff], preferably a benzyloxycarbonyl group, can be mentioned.

The cleavage of protective groups P takes place according to the processes known to one skilled in the art, for example, by catalytic hydrogenolysis, treatment with alkali or with inorganic and/or organic acids, such as, for example, hydrogen halide in glacial acetic acid.

The feedstocks of general formula V, in which $Z^2$ stands for a hydrogen atom, are produced, if they are not commercially available, by the corresponding aminocarboxylic acid esters (see EP 0 405 704) being reduced to alcohols in the way known to one skilled in the art (e.g., J. March, Advanced Organic Chemistry, Third Edition 1985, John Wiley & Sons Press, p. 1095 ff).

The feedstocks of general formula V, in which $Z^1$ stands for a hydrogen atom, can be produced, for example, according to W. C. Vincek, C. S. Aldrich et al., J. Med. Chem. 1981, 24:7–12.

An alternative method of synthesis for triamines of general formula II, in which $Z^2$ stands for a hydrogen atom, uses the borane reduction of amides of general formula VIII

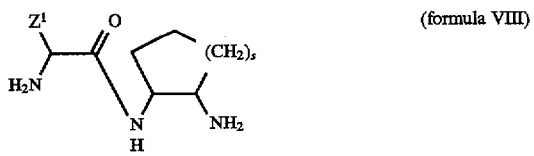

which can be obtained by aminolysis of amino acid esters in a way known in the literature.

The complexing agents of general formula I obtained by the various synthesis methods can be converted to the corresponding metal complexes. It is not necessary to isolate and purify the complexing agents in advance.

The complexing of the metal ions of the elements of the mentioned atomic numbers takes place in the way in which it was disclosed in Patent DE 34 01 052, namely by the metal oxide or a metal salt (for example, nitrate, acetate, carbonate, chloride or sulfate) of the desired element being dissolved or suspended in water and/or a lower alcohol (such as methanol, ethanol or isopropanol) and being reacted with the solution or suspension of the equivalent amount of the complexing agent of general formula I, preferably at temperatures between 40° and 100° C., and then optionally present acid hydrogen atoms of acid groups being substituted by cations of inorganic and/or organic bases, amino acids or amino acid amides.

In this connection, neutralization takes place with the aid of inorganic bases (for example, hydroxides, carbonates or bicarbonates) of, for example, sodium, potassium, lithium, magnesium or calcium and/or organic bases, such as, i.a., primary, secondary and tertiary amines, such as, for example, ethanolamine, morpholine, glucamine, N-methylglucamine and N,N-dimethylglucamine, as well as basic amino acids, such as, for example, lysine, arginine and ornithine.

For production of neutral complex compounds, enough of the desired bases can be added to, for example, the acid complex salts in aqueous solution or suspension to reach the neutral point. The solution obtained can then be evaporated to dryness in a vacuum. It is often advantageous to precipitate the formed neutral salts by adding water-miscible solvents, such as, for example, lower alcohols (methanol, ethanol, isopropanol, etc.), lower ketones (acetone, etc.), polar ethers (tetrahydrofuran, dioxane, 1,2-dimethoxyethane, etc.) and thus to obtain crystallizates that can be easily isolated and readily purified. It has proven especially advantageous to add the desired base as early as during the complexing of the reaction mixture and thus to save a process step.

If the acidic complex compounds contain several free acidic groups, it is often advisable to produce neutral mixed salts which contain both inorganic and organic cations as counterions. This can be done, for example, by the complexing acid being reacted in aqueous suspension or solution with the oxide or salt of the element providing the central ion and optionally being partially mixed with the desired amount of an organic base, the complex salt that is formed being isolated, optionally purified and then, for complete neutralization, being mixed with the necessary amount of inorganic base. The sequence in which the bases are added can also be reversed.

The production of the pharmaceutical agents according to the invention also takes place in a way known in the art, by the complex compounds according to the invention—optionally by adding the additives that are usual in galenicals—being suspended or dissolved in aqueous medium and then the suspension or solution optionally being sterilized. Suitable additives are, for example, physiologically harmless buffers (such as, for example, tromethamine), complexing agents (such as, for example, diethylenetriaminepentaacetic acid) or, if necessary, electrolytes (such as, for example, sodium chloride) or, if desired, calcium, magnesium or zinc salts of organic acids, such as, e.g., ascorbic acid, gluconic acid, diethylenetriaminepentaacetic acid, etc. If suspensions or solutions of the agents according to the invention in water or a physiological salt solution are desired for enteral administration or other purposes, they are mixed with one or more adjuvant(s) (for example, methyl cellulose, lactose, mannitol) and/or surfactant(s), for example, lecithins, Tween®, Myrj® and/or aromatic substance(s), for taste correction (for example, ethereal oils) that are usual in galenicals.

Furthermore, it has proven advantageous to admix the agent of a complexing agent excess (corresponding to EP 0

270 483) e.g., in the form of salts with the same cations, or mixed salts with different cations of inorganic and/or organic bases.

As a result, the compatibility of the contrast medium is further improved. Calcium, magnesium, zinc and/or sodium have been proven to be especially suitable cations.

In principle, it is also possible to produce the pharmaceutical agents according to the invention even without isolating the complex salts. In each case, special care then has to be taken to carry out chelation so that the salts and salt solutions according to the invention are practically free of noncomplexed, toxic metal ions. This can be ensured, for example, with the aid of color indicators such as xylenol orange, by control titrations during the production process. The invention therefore also relates to processes for the production of complex compounds and their salts. Purification of the isolated complex salt remains as a final safety measure.

The pharmaceutical agents according to the invention are administered, depending on the diagnostic formulation of the problem, in doses of 0.1 µmol/kg to 5 mmol/kg, preferably 10 µmol to 0.5 mmol/kg of body weight of the complex salt according to the invention.

When the agents according to the invention are used in the area of NMRdiagnosis, the latter are generally dosed in amounts of 1 µmol–5 mmol, preferably 5 µmol–500 µmol/kg of body weight. Details of use are discussed, e.g., in H. J. Weinmann et al., Am. J. of Roentgenology, 142 (1984) 619.

When the agents according to the invention are used in the area of diagnostic radiology, the latter are generally dosed in amounts of 100 µmol–5 mmol, preferably 250 µmol–1 mmol/kg of body weight. Details of use are discussed, e.g., in Barke, Röntgenkontrastmittel [X-Ray Contrast Media], G. Thieme, Leipzig (1970) and P. Thurn, E. Bcheler—"Einf ührung in die Röntgendiagnostik [Introduction to X-Ray Diagnosis]," G. Thieme, Stuttgart, New York (1977).

The production of the pharmaceutical agents according to the invention also takes place in a way known in the art, by the complex compounds according to the invention— optionally by adding the additives usual in galenicals— being dissolved in an aqueous medium and then this solution optionally being sterilized.

Aqueous formulations with a concentration of 50 µmol/l to 2 mol/l, preferably 100 mmol/l to 1 mol/l, are used in an intravenous injection. In oral use, solutions with a concentration of 0.1 mmol/l to 100 mmol/l are preferably used, and optionally (an) aromatic substance(s) (is) are added for taste correction (e.g., ethereal oils).

In rectal use, solutions in the concentration range mentioned for oral use can also be used. In addition, however, preferably suspensions of the complexes according to the invention with the adjuvants usual in galenicals are also suitable.

The good water solubility and low osmolality of the agents according to the invention make it possible to produce highly concentrated solutions, thus to keep the volume load of the circulatory system within justifiable limits and to offset dilution by bodily fluid. Further, the agents according to the invention exhibit not only high stability in vitro but also surprisingly high stability in vivo, so that release or exchange of the ions—which are toxic in themselves—that are bound in the complexes practically does not take place within the time in which the new contrast media are completely excreted again.

In the administration of the agents according to the invention, the latter can be administered together with a suitable vehicle, such as, e.g., serum or physiological common salt solution and/or together with a protein, such as, e.g., human serum albumin. The dosage in this case is dependent on the type of cellular impairment and the properties of the metal complex used.

The agents according to the invention meet the varied requirements for suitability at contrast media. Thus, they are excellently suited, after enteral or parental administration, for improving the informative value of a nuclear spin tomography image by increasing signal intensity. Further, they show the high effectiveness that is necessary to stress the body with the smallest possible amounts of foreign substances, and the good compatibility that is necessary to preserve the noninvasive nature of the tests. As organspecific contrast media, they are of special value for liver and gallbladder diagnosis. Furthermore, they are very well suited as perfusion agents.

The agents according to the invention can also be used for radiation therapy. Thus, because of the large capture crosssection, complexes of gadolinium are very well suited for neutron capture therapy. If the agent according to the invention is intended for use in the variants of radiation therapy proposed by R. L. Mills et al. [Nature Vol. 336 (1988), p. 787], the central ion must be derived from a MSssbaUer isotope, such as, e.g., $^{57}$Fe or $^{151}$Eu.

The following examples explain the invention without intending it to be limited to the latter.

EXAMPLE 1 a) N-Benzyloxycarbonyl-O-methyl-tyrosine methyl ester
  32.94 g (100 mmol) of N-benzyloxycarbonyl-tyrosine methyl ester is mixed in 200 ml of DMF with 27.64 g (200 mmol) of ground potassium carbonate. 8.96 ml (110 mmol) of iodoethane is instilled in this suspension and stirred overnight at room temperature. The solution is concentrated by evaporation, dispersed between ethyl acetate and water, and the organic phase is mixed with hexane after drying (Na$_2$SO$_4$). The title compound crystallizes out.
  Yield: 32.88 g (92%)
  Flash point: 50°–56° C.
  Analysis:
  Cld: C 67.21 H 6.49 N 3.92
  Fnd: C 66.96 H 6.57 N 3.81 b) N-Benzyloxycarbonyl-3-(4-ethoxybenzyl)-2-aminopropanol 3.18 g (84.8 mmol) of sodium borohydride is added to a solution of 22.14 g (60.6 mmol) of N-benzyloxycarbonyl-O-ethyltyrosine methyl ester (Example 1a) in 150 ml of tetrahydrofuran at room temperature. 27 ml of methanol is instilled in it with stirring within 2 hours. Then, the tetrahydrofuran is distilled off in a vacuum, the residue is taken up in 100 ml of water and extracted three times with 70 ml of ethyl acetate. The combined organic phase is washed with water, dried with sodium sulfate and concentrated. It is recrystallized from ethyl acetate/hexane.
  Yield: 18.7 g (93.7%)
  Flash point: 112°–117° C.
  Analysis:
  Cld: C 69.28 H 7.04 N 4.25
  Fnd: C 69.02 H 7.12 N 4.13 c) N-[2-Benzyloxycarbonylamino-3-(4-ethoxyphenyl) propyl]-cyclohexane-1,2-diaminodihydrochloride
  2.09 ml (26.8 mmol) of methanesulfonyl chloride is slowly instilled in a solution of 8.4 g (25.5 mmol) of the alcohol described in the preceding example and 3.78 ml (27.3 mmol) of triethylamine in 33 ml of tetrahydrofuran at 4° C. with stirring. After two hours, the settled precipitate is filtered off, and the filtrate is instilled in 73.1 g (640 mmol) of 1,2-diamino-cyclohexane. The solution is stirred for four hours at 50° C. and then concentrated in a vacuum. The residue is taken up with water, extracted with ethyl acetate, dried with sodium sulfate and concentrated on a rotary evaporator. The residue is taken up in methanol and acidified at 0° C. with concentrated hydrochloric acid. After suctioning and drying, the product is obtained in the form of colorless crystals (9.7 g; 76.3%) as dihydrochloride.

Analysis:

Cld: C 60.24 H 7.48 Cl 14.22 N 8.43

Fnd: C 59.97 H 7.33 Cl 14.59 N 8.21 d) 8-(4-Ethoxybenzyl)-4,5-tetramethylene-3,6,9-tris(carboxymethyl)-3,6,9-triazaundecanedioic acid, monosodium salt 7.48 g (15.0 mmol) of the triamine described in the preceding example is suspended in 60 ml of methanol, mixed under nitrogen with palladium catalyst (10% Pd on activated carbon) and gassed with hydrogen. After hydrogenation is completed, it is suctioned off from the catalyst, and the filtrate is concentrated by evaporation. The resulting oil is suspended in 150 ml of tetrahydrofuran, mixed with 10.37 g (75 mmol) of potassium carbonate and 7.5 ml of water and, after adding 21.94 g (112.5 mmol) of bromoacetic acid-tert-butyl ester, stirred under reflux for 20 hours. The organic phase is separated, evaporated to dryness, and the resulting oil is chromatographed on silica gel (hexane/ether/triethylamine 70:30:5). The fractions that are concentrated by evaporation (7.94 g; 61%) are dissolved in methanol and, after 9.15 ml of 10N sodium hydroxide solution is added, it is stirred under reflux for 5 hours. Then, it is concentrated by evaporation, and the aqueous solution is adjusted to pH 3 with Amberlite® IR 120 (H$^+$) ion exchanger, and the solution is freeze-dried. The monosodium salt of the complexing agent is obtained.

Yield: 5.57 g (57%)

H$_2$O content: 8.7%

Analysis (relative to anhydrous substance):

Cld: C 53.73 H 6.35 N 6.96 Na 3.81

Fnd: C 53.30 H 6.57 N 6.62 Na 4.09 e) Gadolinium complex of 8-(4-ethoxybenzyl)-4,5-tetramethylene-3,6,9-tris(carboxylatomethyl)-3,6,9-triazaundecanedioic acid, disodium salt 4.0 g (6.63 mmol) of the complexing agent described in Example 1d is dissolved in 40 ml of water and complexed at 80° C. with 1.20 g (3.31 mmol) of Gd$_2$O$_3$. (The adjustment is controlled with a xylenol orange-indicator solution). After cooling, 6.6 ml of 1N sodium hydroxide solution is added, the solution is filtered with a membrane filter (Sartorius cellulose-nitrate 0.1 mm), and the filtrate is freeze-dried.

Yield: 5.55 g (quantitative)

H$_2$O content: 7.3%

Flash point: >300° C.

Analysis (relative to anhydrous substance):

Cld: C 41.59 H 4.39 Gd 20.17 N 5.39 Na 5.90

Fnd: C 41.17 H 4.45 Gd 19.79 N 5.31 Na 5.49

T$_1$-relaxivity (H$_2$O): 5.9±0.53 L/mmol sec

T$_1$-relaxivity (plasma): 9.8±0.84 L/mmol-sec

EXAMPLE 2 a) N-Benzyloxycarbonyl-O-methyl-tyrosine methyl ester 32.94 g (100 mmol) of N-benzyloxycarbonyl-tyrosine methyl ester is mixed in 200 ml of DMF with 27.64 g (200 mmol) of ground potassium carbonate. 15.6 g (110 mmol) of iodomethane is instilled in this suspension and stirred overnight at room temperature. The solution is concentrated by evaporation, dispersed between ethyl acetate and water, and the organic phase is mixed with hexane after drying (Na$_2$SO$_4$). The title compound crystallizes out.

Yield: 31.9 g (93%)

Analysis:

Cld: C 66.46 H 6.16 N 4.08

Fnd: C 66.60 H 6.23 N 3.99 b) N$_a$-Benzyloxycarbonyl-O-methyl-tyrosine-(2-aminocyclohexyl)-amide-hydrochloride 24.0 g (70 mmol) of N-benzyloxycarbonyl-O-methyltyrosine methyl ester is dissolved in 50 ml of methanol and instilled in 420 ml (3.5 mol) of trans-1,2-diaminocyclohexane in about 2 hours. The solution is stirred for 24 hours at room temperature and then evaporated to dryness in an oil vacuum. The oily residue is taken up in ethyl acetate and shaken out with water several times to remove diaminocyclohexane residues. The organic phase is dried (Na$_2$SO$_4$) and mixed in ethyl acetate with 2N hydrogen chloride. The precipitate that is produced after a short time is filtered off and dried at 50° C. in a vacuum.

Yield: 23.0 g (71%)

Analysis:

Cld: C 62.40 H 6.98 C17.67 N 9.10

Fnd: C 61.70 H 7.05 C17.38 N 9.25 c) N-[2-Amino-3-(4-methoxyphenyl)propyl]-cyclohexane-1,2-diamine-trihydrochloride 18.5 g (40 mmol) of N$_a$-benzyloxycarbonyl-O-methyl-tyrosine-(2-aminocyclohexyl)-amide-hydrochloride is suspended in 200 ml of methanol and mixed under nitrogen with palladium on activated carbon (10% Pd) and hydrogenated either in autoclaves or under normal pressure with hydrogen, as desired. After the reaction is completed (about 2–6 hours), it is suctioned off from the catalyst and the filtrate is concentrated by evaporation. The oil obtained is suspended in 320 ml of 1M diborane/tetrahydrofuran complex solution (320 mmol) and stirred under reflux for 48 hours. Then it is cooled in an ice bath, and the reaction is completed by adding 15 ml of methanol. It is stirred for one hour in an ice bath and then hydrogen chloride is introduced; in this process the trihydrochloride precipitates the desired amine. The precipitate is suctioned off and dried on P$_2$O$_5$ Yield: 14.2 g (92%)

Analysis:

Cld: C 49.68 H 7.82 Cl 27.50 N 10.86

Fnd: C 49.21 H 7.70 Cl 28.75 N 10.20 d) 8-(4-Methoxybenzyl)-4,5-tetramethylene-3,6,9-tris(carboxymethyl)-3,6,9-triazaundecanedisic acid, monosodium salt 5.8 g (15 mmol) of the triamine described in the preceding example is suspended in 150 ml of tetrahydrofuran, nixed with 12.4 g (90 mmol) of potassium carbonate and 7.5 ml of water and, after 21.94 g (112.5 mmol) of bromoacetic acid-tert-butyl ester is added, it is stirred under reflux for 20 hours. The organic phase is separated, evaporated to dryness, and the resulting oil is chromatographed on silica gel (hexane/ether/triethylamine 70:30:5). The fractions that are concentrated by evaporation (7.89 g; 62%) are dissolved in methanol and, after 9.15 ml of 10N sodium hydroxide solution is added, it is stirred under reflux for 5 hours. Then, it is concentrated by evaporation and the aqueous solution is adjusted to pH 3 with Amberlite® IR 120 (H⁺) ion exchanger, and the solution is freeze-dried. The monosodium salt of the complexing agent is obtained.

Yield: 5.60 g (59%)

$H_2O$ content: 6.9%

Analysis (relative to anhydrous substance):

Cld: C 52.97 H 6.15 N 7.12 Na 3.90

Fnd: C 53.18 H 6.01 N 7.21 Na 3.47 e) Gadolinium complex of 8-(4-methoxybenzyl)-4,5-tetramethylene-3,6,9-tris(carboxylatomethyl)-3,6,9-triazaundecanedioic acid, disodium salt 4.0 g (6.32 mmol) of the complexing agent described in Example 2d is dissolved in 40 ml of water and complexed at 80° C. with 1.15 g (3.16 mmol) of $Gd_2O_3$. After cooling, 6.3 ml of 1N sodium hydroxide solution is added, the solution is filtered with a membrane filter (Sartorius cellulose-nitrate 0.1 mm), and the filtrate is freeze-dried.

Yield: 5.3 g (quantitative)

$H_2O$ content: 8.4%

Analysis (relative to anhydrous substance):

Cld: C 40.78 H 4.21 Gd 20.53 N 5.49 Na 6.00

Fnd: C 41.02 H 4.11 Gd 19.73 N 5.56 Na 5.71

$T_1$-relaxivity ($H_2O$): 6.2±0.47 L/mmol·sec $T_1$-relaxivity (plasma): 9.4±0.56 L/mmol·sec

EXAMPLE 3 a) N-(2-benzyloxycarbonylamino-3-phenylpropyl)-cyclopentyl-1,2-diamine-dihydrochloride 1.64 ml (21 mmol) of methanesulfonyl chloride is slowly instilled in a solution of 5.7 g (20 mmol) of N-benzyloxycarbonyl-phenylalaninol [Correa et al. Synth. Commun. 21, 1–9 (1991)] and 3.0 ml (21.7 mmol) of triethylamine in 30 ml of tetrahydrofuran at 4° C. with stirring. After 2 hours, the settled precipitate is filtered off, and the filtrate is instilled in 50.1 g (500 mmol) of 1,2-diaminocyclopentane [Jaeger and Blumendal, Z. anorg. Chem. 175, 161 (1928)]. The solution is stirred for 4 hours at 50° C. and then concentrated in a vacuum. The residue is taken up with water, extracted with ethyl acetate, dried with sodium sulfate, and concentrated by evaporation on a rotary evaporator. The remaining oil is taken up in methanol and acidified at 0° C. with concentrated hydrochloric acid. After suctioning off and drying, the product is. obtained in amorphous form.

Yield: 7.1 g (81%)

Analysis:

Cld: C 60.00 H 7.09 Cl 16.10 N 9.54

Fnd: C 59.43 H 7.20 Cl 16.62 N 9.29 b) 8-Benzyl-4,5-trimethylene-3,6,9-tris(carboxymethyl)-3,6,9-triazaundecanedioic acid, monosodium salt 6.6 g (15 mmol) of the triamine described in the preceding example is suspended in 60 ml of methanol, mixed under nitrogen with palladium catalyst (10% Pd on activated carbon), and gassed with hydrogen. After hydrogenation is completed, it is suctioned off from the catalyst and the filtrate is concentrated by evaporation. The resulting oil is suspended in 150 ml of tetrahydrofuran, mixed with 10.37 g (75 mmol) of potassium carbonate and 7.5 ml of water and, after 21.94 g (112.5 mmol) of bromoacetic acid-tert-butyl ester) is added, it is stirred under reflux for 20 hours. The organic phase is separated, evaporated to dryness, and the resulting oil is chromatographed on silica gel (hexane/ether/triethylamine 70:30:5). The evaporated fractions are dissolved in methanol and, after 9.15 ml of 10N sodiuum hydroxide solution is added, it is stirred under reflux for five hours. It is then concentrated by evaporation and the aqueous solution is adjusted to pH 3 with Amberlite® IR 120 (H⁺) ion exchanger, and the solution is freeze-dried. The monosodium salt of the complexing agent is obtained. Yield: 5.4 g (62%)

$H_2O$ content: 6.4%

Analysis (relative to anhydrous substance):

Cld: C 52.84 H 5.91 N 7.70 Na 4.21

Fnd: C 53.17 H 6.07 N 7.62 Na 4.03 c) Gadolinium complex of 8-benzyl-4,5-trimethylene-3,6,9-tris(carboxylatomethyl)-3,6,9-triazaundecanedioic acid, disodium salt 3.67 g (6.3μmmol) of the complexing agent described in Example 3b was dissolved in 40 ml of water and complexed at 80° C. with 1.15 g (3.16 mmol) of $Gd_2O_3$. After cooling, 6.3 ml of 1N sodium hydroxide solution is added, the solution is filtered with a membrane filter (Sartorius cellulose-nitrate 0.1 mm), and the filtrate is freeze-dried.

Yield: 4.97 g (quantitative)

$H_2O$ content: 9.2%

Analysis (relative to anhydrous substance):

Cld: C 39.94 H 3.91 Gd 21.79 N 5.82 Na 6.37

Fnd: C 40.47 H 3.84 Gd 21.31 N 5.62 Na 6.29

$T_1$-relaxivity ($H_2O$): 5.1±0.39 L/mmol·sec $T_1$-relaxivity (plasma): 8.8+0.72 L/mmol·sec

EXAMPLE 4 a) N-(2-Benzyloxycarbonylamino-4-methylpentyl)-cyclohexyl-1,2-diamine-dihydrochloride 1.64 ml (21 mmol) of methanesulfonyl chloride is slowly instilled in a solution of 5.0 g (20 mmol) of N-benzyloxycarbonyl-leucinol [Correa et al. Synth. Commun. 21, 1–9 (1991)] and 3.0 ml (21.7 mmol) of triethylamine in 30 ml of tetrahydrofuran at 4° C. with stirring. After 2 hours, the settled precipitate is filtered off, and the filtrate is instilled in 120 ml (1 mol) of trans-1,2-diaminocyclohexane. The solution is stirred for 4 hours at 50° C. and then concentrated in a vacuum. The residue is taken up with water, extracted with ethyl acetate, dried with sodium sulfate, and concentrated by evaporation on a rotary evaporator. The remaining oil is taken up in methanol and acidified at 0° C. with concentrated hydrochloric acid. After suctioning off and drying, the product is obtained in amorphous form.

Yield: 7.1 g (84%)

Analysis:

Cld: C 57.14 H 8.39 Cl 16.87 N 9.99

Fnd: C 57.43 H 8.20 Cl 16.22 N 9.69 b) 8-(2-Methylpropyl)-4,5-tetramethylene-3,6,9-tris(carboxymethyl)-3,6,9-triazaundecanedioic acid, monosodium salt 6.3 g (15 mmol) of the triamine described in the preceding example is suspended in 60 ml of methanol, mixed under nitrogen with palladium catalyst (10% Pd on activated carbon), and gassed with hydrogen. After hydrogenation is completed, it is suctioned off from the catalyst, and the filtrate is concentrated by evaporation. The resulting oil is suspended in 150 ml of tetrahydrofuran, mixed with 10.37 g (75 mmol) of potassium carbonate and 7.5 ml of water and, after 21.94 g (112.5 mmol) of bromoacetic acid-tert-butyl ester is added, it is stirred under reflux for 20 hours. The organic phase is separated, evaporated to dryness, and the resulting oil is chromatographed on silica gel (hexane/ether/triethylamine 70:30:5). The fractions that are concentrated by evaporation are dissolved in methanol and, after 9.15 ml of 10N sodium hydroxide solution is added, it is stirred under reflux for 5 hours. It is then concentrated by evaporation and the aqueous solution is adjusted to pH 3 with Amberlite® IR 120 ($H^+$) ion exchanger, and the solution is freeze-dried. The monosodium salt of the complexing agent is obtained.

Yield: 5.1 g (61%)

$H_2O$ content: 7.2%

Analysis (relative to anhydrous substance):

Cld: C 50.28 H 6.90 N 8.00 Na 4.37

Fnd: C 49.95 H 7.07 N 7.66 Na 3.96 c) Gadolinium complex of 8-(2-methylpropyl)-4,5-tetramethylene-3,6,9-tris(carboxylatomethyl)-3,6,9-triaazaundecanedioic acid, disodium salt 3.73 g (6.63 mmol) of the complexing agent described in Example 4b is dissolved in 40 ml of water and complexed at 80° C. with 1.20 g (3.31 mmol) of $Gd_2O_3$. (The adjustment is controlled with a xylenol orange-indicator solution.) After cooling, 6.6 ml of 1N sodium hydroxide solution is added, the solution is filtered with a membrane filter (Sartorius cellulose-nitrate 0.1 mm), and the filtrate is freeze-dried.

Yield: 5.02 g (quantitative)

$H_2O$ content: 82%

Analysis (relative to anhydrous substance):

Cld: C 37.6.6 H 4.60 Gd 22.41 N 5.99 Na 6.55

Fnd: C 37.37 H 4.45 Gd 21.79 N 5.61 Na 6.49

$T_1$-relaxivity ($H_2O$): 4.9–0.23 L/mmol·sec $T_1$-relaxivity (plasma): 8.1±0.54 L/mmol·sec

EXAMPLE 5

Gadolinium complex of 8-(4-ethoxycyclohexylmethyl)-4,5-tetramethylene-3,6,9-tris(carboxylatomethyl)-3,6,9triazaundecanedioc acid, disodium salt 5 g (6.41 mmol) of the title compound of Example 1e is dissolved in 50 ml of water, and 3 g of rhodium catalyst (Rh on $Al_2O_3$) is added. The solution is hydrogenated in an autoclave for 48 hours under 10 bars of hydrogen pressure at 40° C. The catalyst is filtered off, and the filtrate is freeze-dried.

Yield: 5.38 g (98.5%)

$H_2O$ content: 7.8%

Analysis (relative to anhydrous substance):

Cld:. C 41.27 H 5.13 Gd 20.01 N 5.35 Na 5.85

Fnd: C 40.95 H 5.29 Gd 19.83 N 5.18 Na 5.41

$T_1$-relaxivity ($H_2O$): 6.2±0.61 L/mmol·sec $T_1$-relaxivity (plasma): 9.7±0.43 L/mmol·sec

We claim:

1. A complex compound of at least one metal ion of an element of atomic numbers 21–29, 42 44 or 58–83 and a complexing agent of formula I in which $Z^1$ and $Z^2$, independently of one another, stand for a hydrogen atom, the radical $-(CH_2)_m-(C_6H_4)_q-(O)_k-(CH_2)_n-(C_6H_4)_l-(O)_r-R$, or the radical $-(CH_2)_m-(C_6H_{10})_q-(O)_k-(CH_2)_n-(C_6H_{10})_l-(O)_r-R$, in which m and n mean a number from 0–5, q, k, l and r mean numbers 0 or 1 and s means numbers 1 or 2, R means a hydrogen atom, an optionally $OR^1$-substituted straight-chain or branched $C_1-C_6$ alkyl radical or a $CH_2-COOR^1$ group, in which $R^1$ means a hydrogen atom, a $C_1-C_6$ alkyl radical or a benzyl group, provided that in each case one of substituents $Z^1$ or $Z^2$ stands for a hydrogen atom and the other does not stand for hydrogen, and that a direct oxygen-oxygen bond is not allowed, and further provided that carboxylic acid groups not required to complex metal ions are optionally present partially or completely as a salt of an amino acid or an amino acid amide or as a salt of an inorganic or organic base.

2. A complex compound according to claim 1, wherein $Z^2$ stands for a hydrogen atom and $Z^1$ stands for a radical $-(CH_2)_m-(C_6H_4)_q-(O)_k-(CH_2)_n-(C_6H_4)_l-(O)_r-R$, or a radical $-(CH_2)_m-(C_6H_4)_q-(O)_k-(CH_2)_n-(C_6H_{10})_l-(O)_r-R$.

3. A complex compound of claim 1, wherein $Z^2$ stands for a hydrogen atom and $Z^1$ stands for a radical isobutyl, n-pentyl, $-CH_2-C_6H_4-OH$, $-CH_2-C_6H_4-OCH_3$, $-CH_2-C_6H_4-O-C_2H_5$, $-CH_2-C_6H_4-O-C_9H_g$, $-CH_2-C_6H_4-O-CH_2-C_6H_5$, $-CH_2-C_6H_5$, $CH_2-C_6H_{10}-O-C_2H_5$, $-CH_2-C_6H_4-O-CH_2-C_6H_4-OCH_3$, $-CH_2-O-CH_2-C_6H_5$ or $-CH_2-C_6H_4-O-CH_2-COOH$.

4. A pharmaceutical agent containing at least one physiologically compatible complex compound according to claim 1, optionally with the additives usual in galenicals.

5. A process for the production of a complex compound of at least one metal ion of an element of atomic numbers 21–29, 42 44 or 58–83 and a complexing agent of formula I in which $Z^1$ and $Z^2$, independently of one another, stand for a hydrogen atom, the radical $-(CH_2)_m-(C_6H_4)_q-(O)_k-(CH_2)_n-(C_6H_4)_l-(O)_r-R$, or the radical $-(CH_2)_m-(C_6H_2)_q-(O)_k-(CH_2)_n-(C_6H_{10})_l-(O)_r-R$, in which m and n mean a number from 0–5, q, k, l and r mean numbers 0 or 1 and s means numbers 1 or 2, R means a hydrogen atom, an optionally OR-substituted straight-chain or branched $C_1$–$C_6$ alkyl radical or a $CH_2$—$COOR^1$ group, in which $R^1$ means a hydrogen atom, a $C_1$–$C_6$ alkyl radical or a benzyl group, provided that in each case one of substituents $Z^1$ or $Z^2$ stands for a hydrogen atom and the other does not stand for hydrogen, and that a direct oxygen-oxygen bond is not allowed, and further provided that carboxylic acid groups not required to complex metal ions are optionally present partially or completely as a salt of an amino acid or an amino acid or as a salt of an inorganic or organic base, which comprises:

a) reacting a triamine of formula II

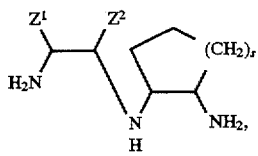

II in which $Z^1$, $Z^2$ and s have the indicated meanings, optionally in the presence of a base, with a compound of formula

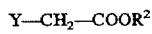

III in which

Y means a leaving group and $R^2$ means an acid protective group or a hydrogen atom, in a polar solvent at −10° C. to 170° C. within 1–100 hours, with protective groups optionally being cleaved; or b) converting a compound of formula IV

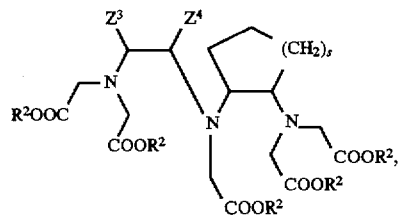

IV in which $R^2$ and s have the indicated meanings and $Z^3$ and $Z^4$ stand, in each case, for a hydrogen atom or radical —$(CH_2)_m$—$(C_6H_4)_q$—OH, provided that one of substituents $Z^3$ and $Z^4$ stands for a hydrogen atom and the other for the indicated radical, to a compound with the radicals indicated for $Z^1$ and $Z^2$, and cleaving acid protective group $R^2$;

and then reacting the complexing agents of formula I obtained according to a) or b) with at least one metal oxide or metal salt of an element of atomic numbers 21–29, 42, 44 or 58–83 and then optionally the carboxylic acid groups not needed for complexing the metal ion(s) are substituted to provide the salt of an inorganic or organic base, amino acid or amino acid amide.

6. Gadolinium complex of 8-(4-ethoxybenzyl)-4,5-tetramethylene-3,6,9-tris(carboxylatomethyl)-3,6,9-triazaundecanedioic acid, a compound of claim 1.

7. A method for diagnostic radiology which comprises administering a complex compound according to claim 1, wherein at least one metal ion is radioactive and is of atomic number 21–29, 42, 44 or 57–83, to enhance the diagnostic radiology.

8. The method of claim 7, wherein the complex compound is administered in a dose of 100 μmol–5 mmol per kg of body weight.

9. The method of claim 7, wherein the diagnostic radiology is for diagnosis of the hepatobiliary system.

10. A method for NMR diagnosis which comprises administering a complex compound according to claim 1, wherein at least one metal ion is of atomic number 21–29, 42, 44 or 58–70, to enhance the NMR diagnosis.

11. The method of claim 10, wherein the complex compound is administered in a dose of 1 μmol–5 mmol per kg of body weight.

12. The method of claim 10, wherein the NMR diagnosis is for diagnosis of the hepatobiliary system.

13. A method for radiation therapy which comprises administering a complex compound according to claim 11, wherein at least one metal ion is radioactive.

* * * * *